US00PP26615P2

(12) United States Plant Patent
Unger

(10) Patent No.: US PP26,615 P2
(45) Date of Patent: Apr. 19, 2016

(54) ***THUNBERGIA* PLANT NAMED 'WESTHUSHIYEL'**

(50) Latin Name: ***Thunbergia gregorii*×*Thunbergia gibsonii***
Varietal Denomination: Westhushiyel

(71) Applicant: Christian Unger, Worms (DE)

(72) Inventor: Christian Unger, Worms (DE)

(73) Assignee: Gartenbau und Spezialkulturen Westhoff GbR, Sudlohn (DE)

( * ) Notice: Subject to any disclaimer, the term of this patent is extended or adjusted under 35 U.S.C. 154(b) by 138 days.

(21) Appl. No.: 13/998,704

(22) Filed: Nov. 26, 2013

(51) Int. Cl.
*A01H 5/02* (2006.01)

(52) U.S. Cl.
USPC ..... Plt./226

(58) Field of Classification Search
USPC ..... Plt./226, 263.1
See application file for complete search history.

*Primary Examiner* — Keith Robinson
(74) *Attorney, Agent, or Firm* — C. A. Whealy

(57) ABSTRACT

A new and distinct cultivar of *Thunbergia* plant named 'Westhushiyel', characterized by its upright and vining plant habit; freely branching habit; dense and bushy plant form; freely flowering habit; yellow orange-colored flowers; and good postproduction longevity.

2 Drawing Sheets

Botanical designation: *Thunbergia gregorii*×*Thunbergia gibsonii*.
Cultivar denomination: 'WESTHUSHIYEL'.

BACKGROUND OF THE INVENTION

The present invention relates to a new and distinct cultivar or *Thunbergia* plant, botanically known as *Thunbergia gregorii*×*Thunbergia gibsonii,* and hereinafter referred to by the name 'Westhushiyel'.

The new *Thunbergia* plant is a product of a planned breeding program conducted by the Inventor in Worms, Germany and Sao Jose do Rio Preto, Brazil. The objective of the breeding program is to create new *Thunbergia* plants with unique flower colors.

The new *Thunbergia* plant originated from a cross-pollination made by the Inventor in Worms, Germany in 2006 of an unnamed selection of *Thunbergia gregorii,* not patented, as the female, or seed, parent with an unnamed selection of *Thunbergia gibsonii,* not patented, as the male, or pollen, parent. The new *Thunbergia* plant was discovered and selected by the Inventor as a single flowering plant from within the progeny of the stated cross-pollination in a controlled environment in Sao Jose do Rio Preto, Brazil in 2007.

Asexual reproduction of the new *Thunbergia* plant by terminal cuttings in a controlled greenhouse environment in Sao Jose do Rio Preto, Brazil since 2007 has shown that the unique features of this new *Thunbergia* plant are stable and reproduced true to type in successive generations.

SUMMARY OF THE INVENTION

Plants of the new *Thunbergia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Westhushiyel'. These characteristics in combination distinguish 'Westhushiyel' as a new and distinct *Thunbergia* plant:

1. Upright and vining plant habit.
2. Freely branching habit; dense and bushy plant form.
3. Freely flowering habit.
4. Yellow orange-colored flowers.
5. Good postproduction longevity.

Plants of the new *Thunbergia* can be compared to plants of the parent selections. Plants of the new *Thunbergia* differ from plants of the parent selections primarily in flower color as plants of the parent selections have orange-colored flowers.

Plants of the new *Thunbergia* can be compared to plants of unnamed selections of *Thunbergia gregorii* known to the Inventor. In side-by-side comparisons conducted in Südlohn-Oeding, Germany, plants of the new *Thunbergia* differed from plants of the unnamed selections in the following characteristics:

1. Plants of the new *Thunbergia* grew faster than plants of the unnamed selections known to the Inventor.
2. Leaves of plants of the new *Thunbergia* were longer and narrower than leaves of plants of the unnamed selections known to the Inventor.
3. Leaves of plants of the new *Thunbergia* were more pubescent than leaves of plants of the unnamed selections known to the Inventor.
4. Flowers of plants of the new *Thunbergia* were yellow orange in color whereas flowers of plants of the unnamed selections known to the Inventor were orange in color.
5. Plants of the new *Thunbergia* had longer peduncles than plants of the unnamed selections known to the Inventor.

BRIEF DESCRIPTION OF THE PHOTOGRAPHS

The accompanying colored photographs illustrate the overall appearance of the new *Thunbergia* plant showing the colors as true as it is reasonably possible to obtain in colored reproductions of this type. Colors in the photographs may differ slightly from the color values cited in the detailed botanical description which accurately describe the colors of the new *Thunbergia* plant.

The photograph on the first sheet comprises a side perspective view of a typical flowering plant of 'Westhushiyel' grown in a container.

The photograph on the second sheet is a close-up view of a typical flowering plant of 'Westhushiyel'.

DETAILED BOTANICAL DESCRIPTION

The aforementioned photographs and following observations, measurements and values describe plants grown during the summer in 18-cm containers in a glass-covered greenhouse in Südlohn-Oeding, Germany and under cultural practices typical of commercial *Thunbergia* production. During the production of the plants, day temperatures ranged from 20° C. to 28° C., night temperatures ranged from 14° C. to 20° C. and light levels ranged from 3,000 to 50,000 lux. Plants were pinched one time about two weeks after planting. Plants were 36 weeks old when the photographs were taken and 20 weeks old when the description was taken. In the following description, color references are made to The Royal Horticultural Society Colour Chart, 2001 Edition, except where general terms of ordinary dictionary significance are used.

Botanical classification: *Thunbergia gregorii*×*Thunbergia gibsonii* 'Westhushiyel'.

Parentage:

- *Female, or seed, parent*.—Unnamed selection of *Thunbergia gregorii,* not patented.
- *Male or pollen parent*.—Unnamed selection of *Thunbergia gibsonii,* not patented.

Propagation:

- *Type*.—By terminal cuttings.
- *Time to initiate roots, summer*.—About 14 days at temperatures about 20° C.
- *Time to initiate roots, winter*.—About 16 to 18 days at temperatures about 20° C.
- *Time to develop roots, summer*.—About 21 to 24 days at temperatures about 20° C.
- *Time to develop roots, winter*.—About 24 to 26 days at temperatures about 20° C.
- *Root description*.—Medium in thickness, fibrous; typically white in color, actual color of the roots is dependent on substrate composition, water quality, fertilizer type and formulation, substrate temperature and physiological age of roots.
- *Rooting habit*.—Freely branching; medium density to dense.

Plant description:

- *Plant and growth habit*.—Upright and vining plant habit; plants require support; vigorous growth habit; rapid growth rate.
- *Branching habit*.—Freely branching habit with lateral branches potentially developing at every node; bushy and dense habit.
- *Plant height*.—About 200 cm.
- *Plant diameter* (*area of spread*).—About 45 cm.

Lateral branch description:

- *Length*.—About 50 cm.
- *Diameter*.—About 1.5 mm to 2 mm.
- *Internode length*.—About 16 cm.
- *Texture*.—Pubescent.
- *Strength*.—Strong, flexible.
- *Color*.—Close to 146B.

Leaf description:

- *Arrangement*.—Opposite, simple.
- *Length*.—About 6 cm.
- *Width*.—About 5.5 cm.
- *Shape*.—Deltoid.
- *Apex*.—Cuspidate.
- *Base*.—Auriculate.
- *Margin*.—Slightly serrate.
- *Aspect*.—Horizontal to somewhat downward.
- *Texture, upper and lower surfaces*.—Pubescent; luster, dull.
- *Venation pattern*.—Pinnate.
- *Color*.—Developing leaves, upper surface: Close to 137B to 137C. Developing leaves, lower surface: Close to 146B. Fully developed leaves, upper surface: Close to 137A; venation, close to 137B. Fully developed leaves, lower surface: Close to 137C; venation, lighter than 137C.
- *Petioles*.—Length: About 4.2 cm. Diameter: About 2 mm. Texture, upper and lower surfaces: Pubescent. Color, upper surface: Close to 138B. Color, lower surface: Close to 138A.

Flower description:

- *Flower type and habit*.—Single axillary salverform flowers; freely flowering habit with numerous flowers developing per plant; flowers face outward to slightly drooping.
- *Natural flowering season*.—Plants flower continuously from April to frost in Germany; plants begin flowering about 12 to 14 weeks after planting.
- *Flower longevity*.—Flowers last about three days on the plant; flowers not persistent.
- *Fragrance*.—None detected.
- *Flower diameter*.—About 5.6 cm by 6 cm.
- *Flower length* (*height*).—About 4.3 cm.
- *Flower buds*.—Length: About 3.7 cm. Diameter: About 1 cm. Shape: Lanceolate to deltoid. Color: Close to 144B.
- *Petals*.—Arrangement: Corolla consists of five petals in a single whorl and fused towards the base. Length: About 5.2 cm. Width: About 2.5 cm. Shape: Roughly spatulate. Apex: Broadly emarginate. Base: Fused. Margin: Entire. Texture, upper and lower surfaces: Smooth, glabrous. Color: When opening and fully opened, upper surface: Close to 14A; color does not fade with development. When opening and fully opened, lower surface: Close to 16A; color does not fade with development. Throat: Close to 25A. Tube: Close to 16A.
- *Sepals*.—Arrangement: About 13 sepals fused towards the base. Length: About 5 mm to 8 mm. Width: About 2 mm. Shape: Lanceolate. Apex: Acute. Base: Fused. Margin: Entire. Texture, upper surface: Smooth, glabrous. Texture, lower surface: Pubescent. Color, upper surface: Close to 145B. Color, lower surface: Close to 145C.
- *Peduncles*.—Length: About 2.1 cm. Diameter: About 2 mm. Angle: About 45° from stem axis. Strength: Strong, flexible. Texture: Pubescent. Color: Close to 144B.
- *Reproductive organs*.—Androecium: Stamen number: About four. Filament length: About 1 cm. Filament color: Close to 12C. Anther shape: Ovate. Anther length: About 6 mm. Anther color: Close to 12C. Amount of pollen: None observed. Gynoecium: Pistil number: One. Style length: About 1.7 cm. Style color: Close to 1C. Stigma appearance: Two-parted. Stigma color: Close to 9A. Ovary color: Close to 144B.

*Seeds and fruits*.—Seed and fruit development has not been observed on plants of the new *Thunbergia*.

Garden performance: Plants of the new *Thunbergia* have been observed to have good garden performance and to tolerate rain, wind and temperatures ranging from about 2° to about 30° C.

Pathogen & pest resistance: Plants of the new *Thunbergia* have not been shown to be resistant to pathogens and pests common to *Thunbergia* plants.

It is claimed:

1. A new and distinct *Thunbergia* plant named 'Westhushiyel' as illustrated and described.

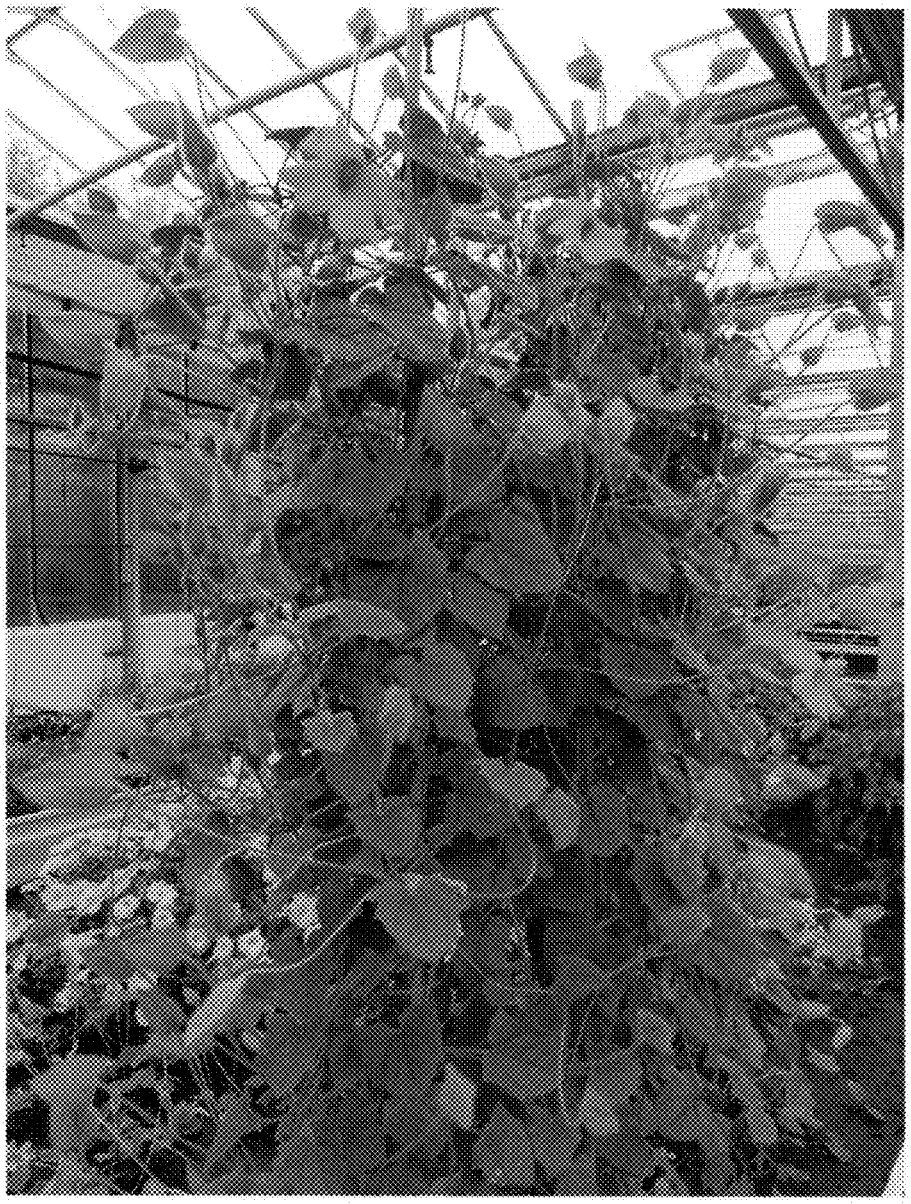

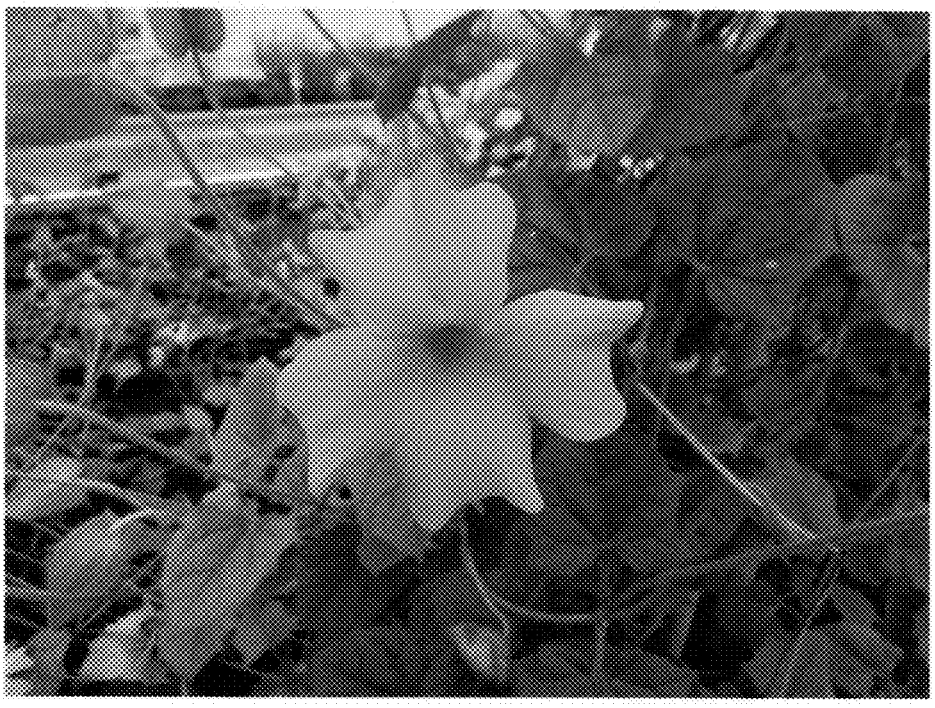

* * * * *